US008512680B2

(12) United States Patent
García-Olmedo Dominguez

(10) Patent No.: US 8,512,680 B2
(45) Date of Patent: Aug. 20, 2013

(54) INJECTABLES IN FOAM, NEW PHARMACEUTICAL APPLICATIONS

(75) Inventor: María Antonia García-Olmedo Dominguez, Granada (ES)

(73) Assignee: BTG International Ltd., London (GB)

( * ) Notice: Subject to any disclaimer, the term of this patent is extended or adjusted under 35 U.S.C. 154(b) by 0 days.

(21) Appl. No.: 11/879,215

(22) Filed: Jul. 16, 2007

(65) Prior Publication Data
US 2008/0031827 A1 Feb. 7, 2008

Related U.S. Application Data

(63) Continuation of application No. 11/342,394, filed on Jan. 30, 2006, now abandoned, which is a continuation of application No. 10/774,071, filed on Feb. 6, 2004, now abandoned, which is a continuation of application No. PCT/ES01/00371, filed on Aug. 8, 2001.

(51) Int. Cl.
A61K 9/12 (2006.01)
A61K 31/00 (2006.01)

(52) U.S. Cl.
USPC .................................. 424/43; 424/400; 514/1

(58) Field of Classification Search
None
See application file for complete search history.

(56) References Cited

U.S. PATENT DOCUMENTS

| | | | |
|---|---|---|---|
| 2,630,183 A | 3/1953 | Foutz | |
| 2,724,383 A | 11/1955 | Lockhart | |
| 3,698,453 A | 10/1972 | Morane et al. | |
| 3,767,085 A | 10/1973 | Cannon et al. | |
| 3,955,720 A | 5/1976 | Malone et al. | |
| 3,970,219 A | 7/1976 | Spitzer et al. | |
| 4,019,657 A | 4/1977 | Spitzer et al. | |
| 4,040,420 A | 8/1977 | Speer | |
| 4,127,131 A | 11/1978 | Vaillancourt | |
| 4,144,126 A * | 3/1979 | Burbidge | 435/235.1 |
| 4,276,885 A | 7/1981 | Tickner et al. | |
| 4,292,972 A | 10/1981 | Pawelchak et al. | |
| 4,328,107 A | 5/1982 | Wright | |
| 4,466,442 A | 8/1984 | Hilmann et al. | |
| 4,538,920 A | 9/1985 | Drake | |
| 4,718,433 A | 1/1988 | Feinstein | |
| 5,048,750 A | 9/1991 | Tobler et al. | |
| 5,064,103 A | 11/1991 | Bennett | |
| 5,071,379 A | 12/1991 | Poizot | |
| 5,084,011 A | 1/1992 | Grady | |
| 5,141,738 A | 8/1992 | Rasor et al. | |
| 5,314,644 A * | 5/1994 | Michelsen et al. | 261/84 |
| 5,368,231 A | 11/1994 | Brunerie | |
| 5,425,366 A | 6/1995 | Reinhardt et al. | |
| 5,425,580 A | 6/1995 | Belller | |
| 5,454,805 A | 10/1995 | Brony | |
| 5,542,935 A | 8/1996 | Unger et al. | |
| 5,556,610 A | 9/1996 | Yan et al. | |
| 5,623,085 A | 4/1997 | Gebhard et al. | |
| 5,656,200 A | 8/1997 | Boettcher et al. | |
| 5,676,962 A | 10/1997 | Garrido et al. | |
| 5,733,572 A * | 3/1998 | Unger et al. | 424/450 |
| 5,902,225 A | 5/1999 | Monson | |
| 6,042,089 A * | 3/2000 | Klein | 261/76 |
| 6,053,364 A | 4/2000 | van der Heijden | |
| 6,086,856 A * | 7/2000 | Saferstein et al. | 424/58 |
| 6,143,276 A * | 11/2000 | Unger | 424/9.3 |
| 6,372,195 B1 * | 4/2002 | Schutt et al. | 424/9.52 |
| 6,536,629 B2 | 3/2003 | van der Heijden | |
| 6,561,237 B1 | 5/2003 | Brass et al. | |
| 6,572,873 B1 | 6/2003 | Osman et al. | |
| 6,605,066 B1 | 8/2003 | Gravagna et al. | |
| 6,730,299 B1 | 5/2004 | Tayot et al. | |
| 6,942,165 B1 | 9/2005 | Osman et al. | |
| RE38,919 E | 12/2005 | Cabrera Garrido et al. | |
| 7,025,290 B2 | 4/2006 | Osman et al. | |
| 7,357,336 B2 | 4/2008 | Osman et al. | |
| 2002/0031476 A1 | 3/2002 | Trevino et al. | |
| 2002/0056730 A1 | 5/2002 | van de Heijden | |
| 2002/0077589 A1 * | 6/2002 | Tessari | 604/82 |

(Continued)

FOREIGN PATENT DOCUMENTS

| | | |
|---|---|---|
| CA | 1 232 837 | 2/1988 |
| DE | 26 08 771 A1 | 9/1976 |

(Continued)

OTHER PUBLICATIONS

"Sulfaproxyline"; The Merck Index, an Encyclopedia of Chemicals, Drugs, and Biologicals, $12^{th}$ Edition; p. 1527; 1996.
$69^{th}$ Medical Seminar Evening of the Van-Swieten Society in the District Hospital of Villach, pp. 1-2, Meeting of Oct. 30, 1959.
Aizman, I. M., "On the Treatment with Sclerosal Agents of Patients with Varicose Lower Extremities", Xupyprus, pp. 46-49, 1964.
Anon, "New Drugs," Australian Prescriber, vol. 25, pp. 20-23 (2002).
Baniel, A. et al., "Foaming Properties of Egg Albumen with a Bubbling Apparatus compared with Whipping," J. Food Science, vol. 62(2): 377-381, 1997.
Baridevic, Dr. Med. Jože, "Varicosclerozation in Phlebological Practice"; The Journal for Doctors, in Clinic and Practice; XXI vol. No. 3, pp. 126-136; Jan. 11, 1989.
Battezzati, M. et al., "Treatment of Lower Limb Varices with Multiple Endermic Ligations and Sclerosant Injections Combined or not with Stripping of the long Saphenous Vein's higher region", Minerva Chirurgica, pp. 936-939, 1952.

(Continued)

Primary Examiner — Daniel Sullivan
Assistant Examiner — Barbara Frazier
(74) Attorney, Agent, or Firm — Finnegan, Henderson, Farabow, Garrett & Dunner, L.L.P.

(57) ABSTRACT

The placing of a drug that is suitable for parenteral administration on bubbles formed with sterile gases produces an exponential increase in its active surface area with a decrease in the diameter of the bubble, modifies the kinetics of its distribution and, thanks to its micronization, increases its therapeutic effect. Furthermore, the echogenicity of the bubbles allows us to follow them on ultrasound after their injection, so that we can visualise the medicament and, thanks to its steerability, can direct it to the selected site or prevent it from reaching undesired areas. This pharmaceutical form is of interest in the treatment of diseases that require a greater local action of the injected drugs than can be achieved with the pharmaceutical forms in current use.

4 Claims, No Drawings

(56) References Cited

U.S. PATENT DOCUMENTS

| | | | |
|---|---|---|---|
| 2002/0091444 A1* | 7/2002 | Yang | 623/11.11 |
| 2002/0101785 A1 | 8/2002 | Edwards et al. | |
| 2004/0156915 A1 | 8/2004 | Harman et al. | |
| 2005/0002873 A1 | 1/2005 | Harman et al. | |
| 2006/0049269 A1 | 3/2006 | Osman et al. | |
| 2006/0062736 A1 | 3/2006 | Wright et al. | |
| 2006/0280690 A1 | 12/2006 | Wright et al. | |
| 2007/0003488 A1 | 1/2007 | Wright et al. | |
| 2007/0003489 A1 | 1/2007 | Wright et al. | |
| 2007/0031345 A1 | 2/2007 | Harman et al. | |
| 2007/0031346 A1 | 2/2007 | Harman et al. | |
| 2007/0104651 A1 | 5/2007 | Wright et al. | |
| 2008/0145401 A1 | 6/2008 | Osman et al. | |
| 2008/0274060 A1 | 11/2008 | Wright et al. | |

FOREIGN PATENT DOCUMENTS

| | | |
|---|---|---|
| DE | 3048744 A1 | 7/1982 |
| DE | 3050812 C2 | 3/1985 |
| DE | 8704600.8 | 11/1987 |
| DE | 3417182 C2 | 1/1989 |
| EP | 0 586875 | 3/1974 |
| EP | 00 11 381 | 5/1980 |
| EP | 0 054 728 A1 | 6/1982 |
| EP | 0 077 752 | 4/1983 |
| EP | 0 123 235 | 10/1984 |
| EP | 0 131 540 | 1/1985 |
| EP | 0 217 582 A2 | 4/1987 |
| EP | 0 324 938 A1 | 7/1989 |
| EP | 0 359 246 | 3/1990 |
| EP | 0 564 505 | 10/1993 |
| EP | 06 13 836 A1 | 9/1994 |
| EP | 0 656 203 A1 | 6/1995 |
| EP | 1 716 871 | 1/1996 |
| EP | 0 997 396 A1 | 5/2000 |
| ES | 2 068 151 | 4/1995 |
| FR | 1 547 768 | 11/1969 |
| FR | 2 672 038 | 7/1992 |
| FR | 2 775 436 | 9/1999 |
| GB | 2 369 996 | 6/2002 |
| JP | 10081895 | 3/1998 |
| JP | H8-235664 | 3/1998 |
| JP | H10-81895 | 3/1998 |
| WO | WO 92/05806 | 4/1992 |
| WO | WO 92/11873 | 7/1992 |
| WO | WO 93/05819 | 4/1993 |
| WO | WO 94/21384 | 9/1994 |
| WO | WO 95/00120 | 1/1995 |
| WO | WO 96/08227 | 3/1996 |
| WO | WO 96/25194 | 8/1996 |
| WO | WO 96/38180 | 12/1996 |
| WO | WO 97/13585 | 4/1997 |
| WO | WO 99/43371 | 9/1999 |
| WO | WO 00/24649 | 5/2000 |
| WO | WO 00/66274 | 11/2000 |
| WO | WO 00/72821 A1 | 12/2000 |
| WO | WO 00/78629 | 12/2000 |
| WO | WO 02/058834 | 8/2002 |
| WO | WO 03/013475 | 2/2003 |
| WO | WO 2004/047969 | 6/2004 |
| WO | WO 2005/115484 | 8/2005 |

OTHER PUBLICATIONS

Bayeux, R. "Comparative Resistance of Dog and Rabbit to Intravenous Injection of Oxygen", Compt. Rend. vol. 156, pp. 1329-1331, 1913.

Belcaro, G. et al., "Treatment of Superficial Venous Incompetence with the Savas Technique", Journal des Maladies Vasculaires (Paris), vol. 16, pp. 23-27, 1991.

Belcaro, G. et al., "Treatment of Superficial Venous Incompetence with a Hemodynamic Technique on an Outpatient Basis: The SAVAS Technique", Vascular Surgery, pp. 32-36, Jan./Feb. 1992.

Belcaro, Gianni; "Micro-sclerotherapy"; Sclerotherapy in Venous Disease; pp. 89-95; 2002.

Bergan, J., "Classic Paper: Nicht-Operative Varizenverödung Mit Varsylschaum," Abstract, Venous digest, 2006.

Bernbach, H. R., "Sclerosing Injections Using the Sigg Method", Phlébologie, vol. 44, No. 1, pp. 31-36, 1991.

Berson, I., "Sclerotization or surgery in the treatment of varicose veins of the inferior extremities", University Clinic for dermato-venerology, Lausanne, pp. 485-190, 1960.

Biegeleisen, H., "Fatty Acid Solutions for the Injection Treatment of Varicose Veins", Annals of Surgery, vol. CV, pp. 610-615, 1937.

Biegeleisen, K. et al., "Inadvertent Intra-Arterial Injection Complicating Ordinary and Ultrasound-Guided Sclerotherapy", Phlebology, vol. 19, pp. 953-958, 1993.

Blenkinsopp, W. K., "Choice of Sclerosant: An Experimental Study", Angiologica, vol. 7, No. 3, pp. 182-186, 1970.

Blenkinsopp, W. K., "Effect of Injected Sclerosant (Tetradecyl Sulphate of Sodium) on Rat Veins", Angiologica, vol. 5, No. 6, pp. 386-396, 1968.

Bock, M.D.H.-D., "Varicosis and its Therapy"; Ärztliche Praxis; XIX Volume, No. 60, pp. 2146-2148; Jul. 29, 1967.

Bodian, E. L., "Techniques of Sclerotherapy for Sunburst Venous Blemishes", J. Dermatol. Surg. Oncol. vol. 11, No. 7, pp. 696-704, Jul. 1985.

Breu, F.X. et al. ;"Duplex Scanning of Lipedema and Lymphedema"; pp. 309-320; Scope on Phlebology and Lymphology; vol. 8; Issue 3/4; Dec. 2001.

Brücke, Von Hans et al., "The combined foam sclerosis of varices", Wiener Medizinische Wochenschrift, vol. 104, No. 1, pp. 111-113, Jan. 1954.

Brugg, Flückiger, P., "Non-Surgical Retrograde Sclerosis of Varicose Veins With Varsyl Foam," Schweizerische Medizinische Wochenschrift No. 48, pp. 1368-1370, 1956.

Butler Studies to Date, "Summary of the Butler gas physiology studies to date (Jun. 13, 2003)", pp. 1-12.

Cabrera, J. et al. ;"Treatment of Varicose Long Saphenous Veins with Sclerosant in Microfoam Form: Long-Term Outcomes"; Phlebology; No. 15, pp. 19-23; 2000.

Cabrera, J. et al.; "Treatment of Varicose Long Saphenous Veins with Sclerosant in Microfoam Form: Long-Term Outcomes"; pp. 293-298.

Cabrera, J. R. et al.; "Extending the Limits of Sclerotherapy: New Sclerosing Products"; Phlébologie; 50 No. 2; pp. 181-188; 1997.

Cabrera, J., "Treatment of Venous Malformations with Sclerosant in Microfoam Form," Arch Dermatol, vol. 139, 2003, 1409-1416.

Cabrera, Juan, "Echo-Sclerotherapy of Long Saphenous Veins and Venous Malformations With Sclerosing Agents in Microfoam Long-Term Outcomes," A Joint meeting of the Canadian Society of Phlebology and the Sclerotherapy Society of Australia, The Transpacific Phlebology Forum, 112, Jun. 27-Jul. 1, 1997, Australia.

Cabrera-Garrido, et al., "New Sclerosing Products: Extending limits in Sclerotherapy," Phlebologie, 50 No. 2, p. 181-188, 1997.

Cabrera-Garrido, J, et al. "New Pharmaceutical Form of Sclerosants: Use in the Treatment of Inoperable Venous Malformations," Poster, May 1997.

Camara, D. S. et al., "The Hemodynamic Effects of the Sclerosant Sodium Morrhuate in Dogs", Surgery—Gynecology and Obstetrics, vol. 161, No. 4, pp. 327-331, Oct. 1985.

Cavezzi, A. et al., "Treatment of Varicose Veins by Foam Sclerotherapy: Two Clinical Series", The Venous Forum of the Royal Society of Medicine and Societas Phlebologica Scandinavica, vol. 17, No. 1, pp. 13-18, Nov. 2002.

Cavezzi, A., "The Use of Sclerosant Foam in Sclerotherapy: possibilities and limits", Management of Venous Disease in the New Millennium, pp. 16-17, Jul. 2000.

Cavezzi, A., "Duplex Guided Sclerotherapy of Long and Short Saphenous Vein With Sclerosing Foam," InFoam Sclerapy State of Art, ed. J.P. Heneriet, Editions Phlébologique Francais pp. 61-71 (2002).

Cho, Kyung J., "Carbon Dioxide Angiography" http://www.emedicine.com/radio/TOPIC870.htm (2008).

Crockett, F. B., "Arterial Complications during Surgery and Sclerotherapy of Varicose Veins", Phlebology, vol. 1, pp. 3-6, 1986.

Davy, A. et al., "Ostial Incompetence—Sclerosis or Resection?", Phlébologie, vol. 39, No. 1, pp. 35-45, 1986.

De L'Academie des Sciences, Conformement a Une Decision de L'Academie, pp. 890-892, Jan. 1930.

Décoppet, R. W., "The Sclerotherapy of Varices with Thrombophilic Patients", Swiss Medical Weekly Journal, 86$^{th}$ year, No. 20, pp. 509-513, May 19, 1956.

DeGroot, W. et al., "Treatment of Varicose Veins: Modern Concepts and Methods", The Journal of Dermatologic Surgery and Oncology, vol. 15, No. 2, pp. 191-198, Feb. 1989.

Dodd, H., "The 'Stripping' Operation for Varicose Veins", The Postgraduate Medical Journal, vol. 31, pp. 73-78, 1955.

Dodd, H., "Varicose Veins and Venous Disorders of the Lower Limb", The Irish Journal of Medicinal Science, Sixth Series, No. 400, pp. 162-174, Apr. 1959.

Dodd, H., "Varicose Veins and Venous Disorders of the Lower Limb", The Proceedings of the Cardiff Medical Society, pp. 28-45, 1962.

Dodd, H., "Vulval Varicose Veins in Pregnancy", Tensile Strength of Arterial Grafts, British Medical Journal, pp. 831-832, Mar. 28, 1959.

Durant, T. et al., "The Safety of Intravascular Carbon Dioxide and its Use for Roentgenologic Visualization of Intracardiac Structures", Annals of Internal Medicine, vol. 47, No. 2, pp. 191-201, Aug. 1957.

Edmonds-Seal, J. et al., "Air Embolism", Anaesthesia, vol. 26, No. 2, pp. 202-208, Apr. 1971.

Efuin, S. et al., "Oxygen Parameters of Blood and Tissues during Intravascular Oxygenation of the Organism", Eksperimental'naya Khirurgiya I Anesteziologiya, vol. 5, pp. 183-186, 1974.

Eichenberger, H., "Results of the Sclerotheraphy of Varicose Veins with Hydroxypolyaethoxy-Dodecan", Zentralblatt für Phlebologie, vol. 8, pp. 181-183, 1969.

Emerson, E. C., "A Reappaisal of the Injection Treatment of Varicose Veins", Angiology the Journal of Vascular Diseases, vol. 14, No. 1, pp. 8-13, Jan. 1963.

English translation of Cabrera-Garrido, J.R. & J.R. Carbrera Garcia-Olmedo, "New Method of Effecting Sclerosis in Varices of the Trunk Veins" Vascular Pathology, vol. 1, No. 4, Oct. 1995.

English translation of Opposition to the European Patent EP 1 180 015 B1, filed Sep. 21, 2006.

Ershov, Y. A. et al., "Variant of an Operation on Enlarged Veins of the Oesophagus and Cardia in Patients with Portal Hypertension Syndrome", Surgery—Monthly Science Practice Journal, Ministry of Health of the Union of Soviet Socialist Republics All-Union Scientific Society of Surgeons, pp. 46-49, Sep. 9, 1991.

Fabi, M. et al., "Un Nuovo Metodo Di Terapia Sclerosante nel Trattamento Delle Varici", L'Arcispedale S. Anna di Ferrera, Book 1, pp. 351-354, 1964.

Farina, M. A. et al., "Outpatient Treatment of Varicose Vein Segments: Two Techniques Compared", Phlébologie, pp. 1070-1071, 1989.

Fegan, G., "The Treatment of Venous Insufficiency During Pregnancy", Varicose Veins—Compression Sclerotherapy, Chapter VII, pp. 93-98, 1967.

Fegan, W. G. et al., "A Modern approach to the injection treatment of varicose veins and its applications in pregnant patients", American Heart Journal, vol. 68, No. 4, pp. 757-764, Oct. 1964.

Fegan, W. G., "Conservative Treatment of Varicose Veins", Progr. Surg. vol. 11, pp. 37-45, 1973.

Fegan, W. G., "Continuous Uninterrupted Compression Technique of Injecting Varicose Veins", Proceedings of the Royal Society of Medicine, vol. 53, No. 7, pp. 837-840, Jul. 1960.

Feied, Craig F., MD, FACEP; "Treatment of all Sizes of Varicose Veins and Spider Veins for Healthy, Beautiful Legs. Mechanism of Action of Sclerosing Agents and Rationale for Selection of a Sclerosing solution"; American Vein Institute; 1996.

Ferguson, L., "Ligation of Varicose Veins, Ambulatory Treatment Preliminary to Sclerosing Injections", Annals of Surgery, vol. CII, pp. 304-314, 1935.

Flückiger, P. et al., "A Contribution to the Techniques for Outpatient Treatment of Varicose Veins", Lecture delivered at the meeting of the German Working Group on Phlebology and the Hamburg Dermatological society on Oct. 20, 1962, Med. Welt 1963, No. 12, pp. 617-621.

Flückiger, P. et al., "Physical and Biological Pathogenetic Components of Varicosis", Schweizer Medizinische Wochenschrift, No. 45, 1963.

Flückiger, P., "Der Erythem-Test im Rahmen der präoperativen Varizenuntersuchung", Praktische Hinweise-Practical Advice, vol. 3, No. 2, pp. 198-199, 1974.

Flückiger, P., "Intraoperative Varicosclerosation with Sodium Tetradecyl Foam in the Babcock Operation", Zentralblatt für Phlebologie, Heft 1, Band 6, pp. 514-518, Feb. 1967.

Foote, R. R., "Varicose Vein Problems in General Practice", The Practitioner—Medical Etiquette, vol. 179, No. 179, pp. 59-66, Jul. 1957.

Foote, R., "Treatment", Varicose Veins, Chapter 5, p. 65 and 86, 1949.

Frugis, E. et al., "Telangieceasia Sclerotherapy of the Lower Limbs", Minerva Dermatologica, Vo. 43, pp. 368-371, 1968.

Frullini, A. et al., "Sclerosing Foam in the Treatment of Varicose Veins and Telangiectases: History and Analysis of Safety and Complications", Dermatol Surg. vol. 28, No. 1, pp. 11-15, Jan. 2002.

Frullini, A., "Sclerosing Foam in the Treatment of Recurrent Varicose Veins"; Foam Sclerotherapy—State of Art; pp. 73-77.

Frullini, A., "Foam Sclerotherapy: a review" Phlebolymphology, No. 40, p. 125-129, 2003.

Frullini, A., "Sclerosing Foam with Polidocanol or Sodium Tertradecyl Sulphate in the Treatment of Superficial Venous Insuffiency"; pp. 289-292.

Galata, G., "Intravenous Injection of Oxygen in Dogs", Archivio di Fisiologia, vol. 21, pp. 331-350, 1923.

Garcia Mingo J., "Foam Medical System," In Foam Sclerotherapy State of the Art, ed. J.P. Heneriet, Editions Phlébologique pp. 45-50 (2002).

Garcia Mingo, J., "Venous Sclerosis with Foam 'Foam Medical System'", Revista Española de Medicina y Ciruia Cosmética, vol. 7, pp. 29-31, 1999.

Garrido, J. Cabrera et al. ; "Elargissement de Limites de la Sclérothérapie: Nouveaux Produits Sclérosants"; Phlébologie; vol. 50, No. 2 ; pp. 181-188 ; 1997.

Garrido, J. Cabrera et al.;"Escleroterapia en Micorespuma : Nuevo Concepto en Escleroterapia. Resultados a Lorgo Plazo."; Revista Panamericana de Flebologia y Lonfologia; No. 34; pp. 29-37; Sep. 1999.

Garrido, Jesús, "Medicine: Microfoam sclerosants against venous illnesses," Medical News, p. 12-16, May 1997.

Gasparini, D., "Therapeutic Embolization in Pulmonary Hemorrhage", Radiologica Interventistica, vol. 77, pp. 223-229, 1989.

German Nullity Action Complaint filed Jul. 27, 2001.

German Nullity Action English Translation of the Reply to appeal dated Feb. 12, 2004.

German Nullity Action English Translation of the Substantiation of Appeal to the Federal Court of Justice on Sep. 26, 2003.

German Nullity Action First Brief filed Dec. 3, 2001.

German Nullity Action Kreusler Brief filed Jan. 27, 2003.

German Nullity Action Supplemental Brief filed Dec. 31, 2002.

Gerson, L., "The Treatment of Varicose Veins, A Critical Study of Choice of Method", Angiology, The Journal of Vascular Diseases, vol. 13, No. 16, pp. 260-264, 1962.

Gilje, O., "Injection Treatment of Varicose Veins", Den norske Legeforening, No. 17, pp. 1380-1381, Sep. 1963 and translation into English.

Gillesberger, W., "The Equipment of the Dermatologist Working in the Field of Phlebology", the Journal for Skin Diseases; vol. 44 (18), pp. 669-674; 1969.

Goldberg, D., "Nd : YAG Laser Treatment of Spider Veins"; pp. 284-288.

Goldman, M. P. et al., "Continuing Medical Education (Dermatologic Surgery), Treatment of Telangiectasia: A review", Journal of the American Academt of Dermatology, vol. 17, No. 2, part 1, pp. 167-182, Aug. 1987.

Goldman, M. P., "Sclerotherapy Treatment of Varicose and Telangiectatic Leg Veins", Clinical Methods for Sclerotherapy of Varicose Veins, pp. 274-275, 290, 312 and 323, 1991.

Goldman, M. P., M.D., "Variations on Injection Technique", Sclerotherapy: Treatment of Varicose and Telangiectatic Leg Veins, pp. 274-275, 290, 312-323, 1991.

Gorisch, V. et al., "Appearance of intravenously given radioactive oxygen in expired air", Naunyn-Schmiedebergs Archiv fuer Experimentelle Pathologie and Pharmakologie, vol. 238, pp. 106-107, 1960.

Gorisch, V. et al., "Expiration of labeled oxygen after intravenous insufflation", Medicina Experimentalis, vol. 1, pp. 333-338, 1959.

Graff, T. et al., "Gas Embolism: A Comparative Study of Air and Carbon Dioxide as Embolic Agents in the Systemic Venous System" Am. J. Obst. & Gynec., Aug. 1959 p. 259-265.

Grondin, L., "Echosclerotherapy of Saphenous Axis with Microfoam Agents," Abstracts form the 13th Annual Congress of the American College of Phlebology, Nov. 1999.

Grosse-Brockhoff, F. et al., "Carbon Dioxide as a Contrast Medium for use in Radiology of the Heart and Blood Vessels," Fortschritte Auf Dem Gebiete Der Röntgenstrahlen Und Der Nuklearmedizin, 1957, 86(3): 285-291.

Günther, E., "On the indication and method of sclerotherapy", Ärztliche Fortbildung, vol. 55, Brochure 22, pp. 1296-1298, Nov. 1961.

Gyorgy, B., "Visszérbetegség Másodlagos Szövödményeinek Kelelése", Orvosi Hetilap, vol. XCIX, No. 35, pp. 1215-1218, 1958.

Handley, R. S., "The Treatment of Varicose Veins", The Practitioner—Diseases of the Veins, No. 993, vol. 166, pp. 228-235, Mar. 1951.

Harkins, H. et al., "Embolism by Air and Oxygen: Comparative Studies", Proceedings of the Society for Experimental Biology and Medicine, vol. 32, pp. 178-181, 1934-35.

Hauer, G., "Diagnostic and Surgical Treatment of Varicose Veins", Herz, vol. 14, No. 5, pp. 274-282, 1989.

Hauser, A. et al., "Prophylaxis of Phlebitis and Treatment of Varices During Pregnancy", Schweizerische Medizinische Wochenschrift, 84th year, No. 1, pp. 13-14, Jan. 2, 1954.

Heinrich, F., "Venous Thrombosis and Pulmonary Embolism during Pregnancy and the Puerperium"; pp. 299-308.

Henriet, J. P. "One Year of Daily Application of Sclerotherapy (Reticular Veins and Telangiectases) Using Polidocanol Foam: Feasibility, Results, Complications," Phlebologie, 1997, 50, No. 3, 355-360, Britain.

Henriet, J. P., "History of Foam," In Foam Sclerotherapy State of the Art, ed. J.P. Heneriet, editions Phlébologique Francais pp. 13-15 (2002).

Henschel, O.,"Die Varizenverördening—Verördungstherapie mit Aethoxysklerol—Kreussler"; p. 22; 1968.

Hess, H., "Digital Subtraction Arteriography with Carbon Dioxide: an alternative to arteriography of the extremities with iodine-containing contrast media," Forlschr. Röntgenstr., 1990, 153(3): 233-238.

Heyerdale, W. et al., "Management of Varicose Veins of the Lower Extremities", Annals of Surgery, vol. 114, pp. 1042-1049, 1941.

Hobbs, J. T., "Compression Sclerotherapy in Venous Insufficiency", Acta Chir Scand Suppl., vol. 544, pp. 75-80, 1988.

Hobbs, J. T., "Surgery and Sclerotherapy in the Treatment of Varicose Veins", Arch. Surg. vol. 109, pp. 793-796, Dec. 1974.

Hobbs, J. T., "The Treatment of Varicose Veins—A Random Trial of Injection-Compression Therapy Versus Surgery", Brit. J. Surg., vol. 55, No. 10, pp. 777-780, Oct. 1968.

Hobbs, J. T., "The Treatment of Varicose Veins in Dublin", Clinical Supplement, pp. 57-60, 1961.

Hobbs, J. T., "Varicose Veins", ABC of Vascular Diseases, vol. 303, pp. 707-710, Sep. 21, 1991.

Hobbs, J., "Surgery or Sclerotherapy for Varicose Veins", Archs. Surg. Nol. 109, p. 793, 1974.

Holzegel, K., "On Sclerosing Agents for Varicose Veins", Zentralblatt für Phlebologie, vol. 9, pp. 43-53, 1970.

Hördegen, K. M., "Conconitant Circulatory Problems in the Arteries or immobility in mostly older patients make outpatient treatment of ulcers more difficult", Schweiz. Med. Wschr., vol. 119, No. 37, pp. 1264-1269, 1989.

Jaeger, F., "Primary or Secondary Varicose Veins", Die Medizinische, No. 36, pp. 1237-1340, Sep. 1955.

Jaeger, F., "Varcose Veins", Deutsche Medizinische Wochenschrift, vol. 83, No. 30, p. 1295, Jul. 1958.

Jaeger, P., "The Current Treatment Standard for Crural Ulcer and Varices", Deutsche Medizinische Wochenschrift, vol. 77, No. 14, pp. 421-425, Apr. 4, 1952.

Jausion, H., "Glycerine Chromee et Sclerose des Ectasies Veineuses", La Presse Medicale, No. 53, pp. 1061-1063, May 5, 1933.

Judgment dated May 22, 2007, in German Nullity Appeal Proceedings BTG International Ltd., X ZR 56/03.

Jung, R., "Injection Treatment of Varicose Veins", Praxis, pp. 195-198, 1950.

Karmazsin, L. et al., "Experimental Study of Lipid Peroxidation Following Intravenous Oxygen", Kiserletes Orvostudomany, vol. 39, pp. 342-348, 1987.

Knight, R. M. et al., "Ultrasonic Guidance of Injections into the Superficial Venous System", Phlebology, pp. 339-341, 1989.

Koistinen, P., "Eräitä näkökohtia alaraajojen laskimon-laajentumien hoidosta ja ennusteesta", Duodecim, vol. LXXII, No. 12, pp. 1000-1015, 1956.

König, T. & Krasmy, R., "CO2 Angiography: Measurement of vascular gas filing and evaluation of parameters influencing gas injection using a circulatory system model," Biomedizinische Technik, 1991, 34(11): 266-270.

Kunkel, F., "Medical Journal of Munich", 95th year of edition, vol. 30, No. 44, p. 53, 1953.

Leidinger, H., Sclerosation with air-block technique (Varicocid plus Varicocid foam), Medizinische Klinik, pp. 1183-1184, 1954.

Lemaire, A. et al., "Effect of Intra-arterial oxygen injection on blood cholesterol", Therapie, vol. 13, pp. 395-399, 1958.

Leonhardt, H., "On the Treatment of Extensive Formation of Varicose Veins with Ligature of the v. Saphena and Varicoid Injection Through Distally Inserted Ureteral Catheter", Ärztliche Wochenschrift, vol. 7, No. 3, pp. 56-58, Jan. 1952.

Leu, H. J. et al., "The Combined Surgical-Sclerotic Ambulatory Treatment of Saphenous Varicose Veins", Schweizerische Rundschau für Medizin, vol. 1, No. 61, pp. 1360-1364, Oct. 31, 1972.

Leu, H. J. et al., "The Modern Conception of Therapy of Varicose Veins", Angiology, The Journal of Vascular Diseases, vol. 15, No. 9, pp. 371-378, Sep. 1964.

Leun, W. et al., "The Limits and Risks of the Sclerotherapy of Varicose Veins", German Medical Weekly Journal, No. 7, pp. 257-260, Feb. 18, 1955.

Lilly, G. D. et al., "An Evaluation of "High" Lumbar Sympathectomy in Arteriosclerotic Circulatory Insufficiency of the Lower Extremities", Surgery, Original Communications, vol. 35, No. 1, pp. 40-44, Jan. 1954.

Lockhart-Mummery, H. E. et al., "Varicose Ulcer—A Study of the Deep Veins with Special Reference to Retrograde Venography", The British Journal of Surgery, vol. XXXVIII, No. 151, pp. 284-295, Jan. 1951.

Luke, J. C. et al., "Factors in the Improvement of Results in Varicose Vein Surgery", Improved Vein Surgery, Canadian Journal of Surgery, vol. 6, No. 2, pp. 145-148, Apr. 1963.

Lunkenheimer, Dr. E., letter to Chem. Fabrik Kreussler & Co.; Mar. 20, 1967.

Maarz, "Nil nocere!: Life-Threatening anaphylactic Incidents in Connection with Sclerosing of Varicose Veins", Munchener Medizinische Wochenschrift, vol. 27, No. 35, 1954.

MacPherson, A. I. S., "The Treatment of Varicose Veins", The Practitioner—Diseases of the Veins, vol. 183, No. 1093, pp. 11-18, Jul. 1959.

Mairano, M., "Metodo combinato chirurgico-sclerosante o metodo sclerosante semplice nel trattamento delle varici essenziali?" Minerva Chirurgica, vol. VI, No. 16, pp. 244-247, May 1951.

Malyugin, "Influence exerted on the liver by the intraportal administration of oxygen", Farmakologiya, vol. 37, No. 2, pp. 183-186, 1974.

Marmasse, J., "Sclerosing Injections in the Saphenofemoral Junction of the Saphenous Veins. Exploration, Injection, Critique.", La Semaine des Hopitaux, vol. 36, No. 17, pp. 1086-1095, Apr. 1960.

Masaki, M. et al., "The destructive effects of sclerosant ethanolamine oleate on mammalian vessel endothelium", Gastroenterologia Japanica, vol. 25, No. 1, pp. 230-235, Feb. 1990.

Material Safety Data Sheet for polydocanol (2009).

Mathiesen, F. R., "Treatment of Varicose Veins—Retrograde Injection or Communicant Resection", Nordisk Medicin, vol. 64, No. 48, pp. 1525-1529, 1960.

Mauer, W., "Is the sclerosing therapy in the case of varicosis advisable in practice?", Therapie der Gegenwart, Issue 5, pp. 242-245, May 1961.

May, R., "Impairments and Risks of the Treatment of Varicose Veins", Münchener Medizinische Wochenschrift, No. 1, pp. 13-16, Jan. 1956.

Mayer, G., "The Treatment of Varicose Veins from the point of View of Sclerotherapy, in particularly on the Basis of Varicophtine", Münchener Medizinische Wochenschrift, vol. 16, No. 20, Columns 1037-1039, Jan. 1952.

Mayer, H. et al., "Angiology: The Aetiology and Treatment of Varicosities of the Lower Extremity," Chirurgische Praxis, pp. 521-528, 1957.

Medelman, J. P., "History of the Section on Radiology", The Journal of the American Medical Association, vol. 178, No. 8, pp. 785-911, Nov. 25, 1961.

Methiesen, F. R., "Subclinical Deep Venous Damage After Sclerosing Injection Demonstrated by Phlebography", Acta Chirurgica Scandinavica, vol. 118, Fasc. 2, pp. 155-166, 1959.

Meyer's Encyclopedia, 5$^{th}$ Edition, 1895, vol. 15, pp. 386.

Min, Robert J., "Transcatheter Duplex Ultrasound Guided Sclerotherapy"; Abstracts from the 13$^{th}$ Annual Congress of the American College of Phlebology; Nov. 10-13, 1999.

Minga, Javier Garcia, "Venous sclerotherapy with foam: 'Foam Medical System'," p. 1-3, 1999.

Miserey, G. et al., "Sclerose Sous Echographie Dans Certaines Zones a Risques", Phlebologie, vol. 44, No. 1, pp. 85-96, 1991.

Monfreux, A., "Sclerosant Treatment of Saphenous Truncs and Their Large Calibre Collaterals by the MUS Method," Phlebologie, 1997, 50, No. 3, 351-353.

Moore, R. M. and C.W. Braselton, "Injections of Air and of Carbon Dioxide into a Pulmonary Vein" Annuals of Surgery, Aug. 1940 p. 212-218.

Moore, R. M. et al., "Injections of Air and Carbon Dioxide into a Pulmonary Vein", Annals of Surgery, vol. 112, pp. 212-218, 1940.

Morsiani, E. et al., "Effect of Intravenous and Intreperivenous Injections of Sclerosants (Sodium Tetradecyl Sulfate and Hydroxy Polyethoxy Dodecan) on the Rat Femoral Vein", Resesarch in Experimental Medicine, vol. 187, pp. 439-449, 1987.

Moszkowiez, L., "Treatment of Varicose Veins with Sugar Injections, combined with vein ligation", Zentralblatt fur Chirurgie, No. 28, pp. 1731-1736, 1927.

Muller, R., "The Ambulatory Phlebectomy", Therapeutische Umschau, vol. 49, No. 7, pp. 447-450, 1992.

Myers, H. L., "Injection Therapy for Varicose Veins", The Journal of Family Practice, vol. 3, No. 5, pp. 531-534, 1976.

Nullity Appellant's statement dated Apr. 4, 2007 in German Nullity Appeal Proceedings BTG International Ltd., 114-59/03.

Ochsner, A. et al., "Comparative Value of Intravenous Sclerosing Substances", Archives of Surgery, vol. 29, No. 3, pp. 397-416, Sep. 1934.

Oden, H. G., "Can the Results of the Treatment of Varicose Vains and Ulcus Cruris be Improved?", Münchener, Medizinische Wochenschrift, vol. 22, No. 8, pp. 364, Jan. 1952.

Office Action dated Nov. 14, 2008 for U.S. Appl. No. 10/536,862.

Olivier, C. et al., "Reinterventions Performed on Primary Varicose Veins of the Lower Limbs", La Presse Medicale, vol. 74, No. 26, pp. 1355-1360, May 25, 1966.

Olivier, C., "Surgical Treatment of Trophic Ulcers of the Inferior Members", Journal de Chirurgie, vol. 78, No. 2, pp. 157-174, Oct. 1959.

Oppenheimer, M. J. et al., "In vivo Visualization of Intracardiac Structures with Gaseous Carbon Dioxide—Cardiovascular-Respiratory Effects and Associated Changes in Blood Chemistry", American Journal of Physiology, vol. 186, pp. 325-334, Jul.-Sep. 1956.

Orbach, E. J. et al., "Investigation of the Different Injection Techniques in the Sclerotherapy of Varicose Veins by Minidose and Differential Pressure Phlebography", VASA, vol. 4, No. 2, pp. 175-183, 1975.

Orbach, E. J. et al., The Thrombogenic Property of Foam of a Synthetic Anionic Detergent (Sodium Tetradecyl Sulfate N.N.R), Thrombogenic Property of a Detergent, vol. 1, pp. 237-243, 1950.

Orbach, E. J. et al.; "The Thrombogenic Property of Foam of a Synthetic Anionic Detergent (Sodium Tetradecyl Sulfate N.N.R.)", Angiol 1, pp. 237-243; 1950.

Orbach, E. J., "A Unified Approach to the Therapy of Varicosities", Angiology, vol. 15, No. 12, pp. 558-560, Dec. 1964.

Orbach, E. J., "Allergenic Tissue Reaction of Catgut, an Aid for the Obliteration of Varicose Veins", The Journal of the International College of Surgeons, vol. XXII, No. 6, pp. 707-710, Dec. 1954.

Orbach, E. J., "Article on Treatment of Teleangiectasias", Zentralblatt für Phlebologie, Heft 1, Band 3, pp. 4-7, Feb. 15, 1964.

Orbach, E. J., "Contributions to the Therapy of the Varicose Complex", Journal of the International College of Surgeons, pp. 765-771, Jun. 1950.

Orbach, E. J., "Controversies and Realities of Therapy for Varicosis", International Surgery, vol. 62, No. 3, pp. 149-151, Mar. 1977.

Orbach, E. J., "Has Injection Treatment of Varicose Veins Become Obsolete?", The Journal of American Medical Association, vol. 166., No. 16, pp. 1964-1966, Apr. 19, 1958.

Orbach, E. J., "Hazards of Sclerotherapy of Varicose Veins—their prevention and treatment of complications", VASA, vol. 8, No. 2, pp. 170-173, 1979.

Orbach, E. J., "Misconceptions and Pitfalls in Sclerosing Therapy of Varicose Veins", Angiology—The Journal of Vascular Diseases, vol. 14, No. 11, pp. 552-555, Nov. 1963.

Orbach, E. J., "Reappraisal of the Sclerotherapy of Varicose Veins", Angiology—The Journal of Vascular Diseases, vol. 8, No. 6, pp. 520-527, Dec. 1957.

Orbach, E. J., "Sclerotherapy of Varicose Veins—Utilization of and Intravenous Air Block"; American Journal of Surgery; vol. LXVI, No. 3, pp. 362-366; Dec. 1944.

Orbach, E. J., "The importance of removal of postinjection coagula during the course of sclerotherapy of varicose veins", VASA, vol. 3, No. 4, pp. 475-477, 1974.

Orbach, E. J., "The Place of Injection Therapy in the Treatment of Venous Disorders of the Lower Extremity—with Comments on its Technique", Presented at the Annual Meeting of the International College of Angiology, London, pp. 18-23, Jul. 1965.

Orbach, E. J., "The Place of Injection Therapy in the Treatment of Venous Disorders of the Lower Extremity—with Comments on its Technique", Angiology—The Journal of Vascular Diseases, vol. 17, No. 1, pp. 18-23, Jan. 1966.

Orbach, E., "Leg Ulcers of Vascular Origin and Their Therapy" The American Journal of Surgery, vol. LXXXI, No. 5, pp. 568-572, May 1951.

Orbach, J., "Varicose Veins", Medical Trial Technique Quarterly, vol. XIV, No. 4, pp. 27-38, Jun. 1968.

Ouvry, P. A., "Telangiectasia and Sclerotherapy", J. Dermatol. Surg. Oncoo. vol. 15, No. 2, pp. 177-181, Feb. 1989.

Ouvry, P. et al., "Aétoxisclerol: First Impressions", Phlébologie, vol. 31, No. 2, pp. 75-77, 1978.

Ouvry, P. et al., "Le Traitement Sclérosant des Télangiectasies des Membres Inférieurs", Phlébologie, vol. 35, No. 1, pp. 349-359, 1982.

Ouvry, P. et al., "Sclerosant Treatment of Telangiectasias of the Lower Limbs", Phlébologie, vol. 32, No. 4, pp. 365-370, 1979.

Ouvry, P. et al., "Sclerotherapy of Perforating Veins", Phlébologie, vol. 40, No. 3, pp. 633-641, 1987.

Pfosi, Von H., "On the Sclerosing Treatment of Varicose Veins", Schweizerische Rundschau für Medizin—Revue Suisse de medecine, 54$^{th}$ year of Edition, No. 29, pp. 868-871, Jul. 22, 1965.

Piulaches, P. et al., "Pathogenic Considerations on Varicose Veins Developed in Pregnancy", Lyon Chirurigical, Bulletin official de la Socirte de Chriurgie de Lyon, vol. 47, No. 3, pp. 263-278, Apr. 1952.

Piulachs, P. et al., "Pathogenic Study of Varicose Veins", Angiology, The Journal of Vascular Diseases, vol. 4, No. 1, pp. 59-100, Feb. 1953.

Postma, G. J., "Ethanolamine Oleate Injection: Therapeutic and Pharmaceutical Aspects", Journal of the Dutch Association of Hospital Pharmacists, 8$^{th}$ year, Issue 3, pp. 84-91, Sep. 1992.

Rabe, E. et al.; "Guidelines to Sclerosing Treatment of Varicose Veins"; Leitlinien der DGP, Phlebologie; vol. 6, pp. 154-158; 2001.

Ramstad, K. R. et al., "Operative Treatment of Varicose Veins—Follow-up of Patients Treated with ligature/injection and "Stripping" respectively", Tidsskrift for Den Norske Laegeforening, No. 10, pp. 623-625, May 1959.

Rappert, E., "The achievements of surgical therapy of varicose veins and leg ulcers?", Die Medizinische, No. 22. pp. 906-914, May 1958.

Rappert, E., "The Therapy of Varicose Crural Ulcers", Wiender Medizinische Wochenschrift, vol. 106, No. 48, pp. 999-1000, Dec. 1, 1956.

Rappert, E., "The treatment of varicose veins following a phlebitis and thrombosis", Winer Medizinische Wochenschrift, No. 4, pp. 100-101, 1957.

Rauhs, R., "Sclerotherapy, its indications and treatment successes", Klinische Medizin, Issue 1, pp. 5-12, Jan. 1961.

Ree, A., "The Treatment of Varicose Veins with Etamolin Foam"; Acta Dermato-Venereologica; vol. 39, pp. 428-432; 1959.

Ree, A., "Varicose Vein Treatment with Foam of Etamolin", Dansk Lægeforening, No. 12-15, pp. 452-453, Jun. 1955.

Reiner, L., "The Activity of Anionic Surface Active Compounds in Producing Vascular Obliteration", Surface Active Sclerosing Agents, Proceedings of the Society for Experimental Biology and Medicine, vol. 62, pp. 49-54, May-Jun. 1946.

Reinharez, D., "Perforating Vein Sclerosis Technique", Ph Phlébologie, vol. 31, No. 2, pp. 69-74, 1978.

Robertson, C. S., "A Study of the Local Toxicity of Agents Used for Variceal Injection Sclerotherapy," HPB Surgery, 1989, vol. 1, pp. 149-154.

Rogge, H., "On the dangers of sclerosing recurring varicose veins", Deutsche Medizinische Wochenschrift, No. 9, p. 301, 1950.

Rompp, Dr. Hermann; "Varsyl"; Chemie Lexikon, Vierte Vollig Neu Bearbeitete Auflage; p. 4649 ; 1958.

Rowden-Foote, R., "Varicose Veins Hemorrhoids and Other Conditions—Their Treatment by Injection"; London, H.K. Lewis & Co. Ltd.; pp. 13-45, 106-119; 1944.

Sadoun, S., "Sclerosing Foam: Material and Methods," In Foam Sclerotherapy State of the Art, ed. J.P. Heneriet, editions Phlébologique Francais pp. 25-32 (2002).

Salamon, Z., "Sclerosing Agents—Toxicity and Mechanism of Action", Wiadomosci Lekarskie, vol. 26 (19), pp. 1819-1822, 1973.

Santler, R., "Sclerosing Therapy of Varicose Veins", Weiner Klinische Wochenschrift, Issue 24, No. 76, pp. 431-434, Jun. 12, 1964.

Savonuzzi, G. et al., "A Therapeutic Method that Combines Sclerosing Agents and Anticoagulants for varicose diseases of the lower limb", Minerva Medical, vol. XLVIII, No. 24, pp. 1124-1126, Mar. 24, 1957.

Schadeck, M. et al., "Echotomographie de la Sclerose", Phlebologie, vol. 44, No. 1, pp. 111-130, 1991.

Schadeck, M., "Duplex Controlled Sclerosing Treatment of the Great Saphenous Vein"; Phlebol; vol. 25, pp. 78-82; 1996.

Schadeck, M., "Sclerotherapy in the Child", Phlébologie, vol. 45, No. 4, pp. 509-512, 1992.

Schadeck, M., "Ultrasound-controlled Sclerotherapy of the Great Saphenous Veins"; Phlébologie; vol. 46, No. 4, pp. 673-682, 1993.

Schmier, A., "Clinical Comparison of Sclerosing Solutions in Injection Treatment of Varicose Veins, Delayed Slough: Recurrence of Varices", The American Journal of Surgery, vol. XXXVI, No. 1, pp. 389-397, Apr. 1937.

Schneider, H. O., "Varix Treatment with Modern Sclerosing Agent", Zeitschrift für Haut and Geschelchtskrankheiten, Band XXXIII, Heft No. 5, pp. 163-166, Sep. 1962.

Schneider, W. et al., "On the histology of the Varicose Injection Treatment in People with new Injection Treatment Agents", Archive for Clinical and Experimental Dermatology, vol. 220, pp. 234-249, 1964.

Schörcher, F., "For the Practice Varicose Veins and Deep Chronic Crural Thrombosis", Münchener Medizinische Wochenschrift, No. 41, pp. 1354-1358, Oct. 14, 1955.

Scneider, W., "Regarding non-operative varicosclerosation", Die Medizinische Welt, vol. 3, No. 5, pp. 225-227, Feb. 1961.

Seeger, J., et al., "Carbon Dioxide Gas as an Arterial Contrast Agent," Annals of Surgery, vol. 217, No. 6, p. 688-698, 1993.

Shafi, Z. B. et al., "Factors Affecting High Shear Preparation of Albumin Microspheres", Pharmaceutical Sciences Research Group, p. 144P, 1990.

Sica, M., "Ultrasound Appearance of Sclerosing Foam," In Foam Sclerotherapy State of the Art, ed. J.P. Heneriet, editions Phlébologique Francais pp. 85-88 (2002).

Sicard, P., "Sclerosing Treatment of Varicose Veins of the Lower Limbs", Therapeutics, vol. 36, No. 2, pp. 127-129, Feb. 1960.

Sigg, "Regarding treatment of varicose veins and their complications", Dermatologica, vol. 100, p. 317, 1950.

Sigg, K. et al., "New Sclerosing Substances for Varicose Veins", Munchener Medizinische Wochenschrift, Issue 1, Mar. 1961.

Sigg, K. et al., "Prophylaxis of Thrombosis during Gravidity", Die Medizinische, No. 12, pp. 420-423, Jan. 1957.

Sigg, K. et al., "Treating varices with Sclerotherapy", Langenbacks Arch. Chir., vol. 347, pp. 231-234, 1978.

Sigg, K., "A Good Prophylaxis of Thrombosis during Pregnancy, delivery and childbed as well as for Operations can Prevent the Thrombo-Embolism", Munchener Medizinische Wochenschrift, vol. 99, No. 17, p. 581 and 610-613 Apr. 1957.

Sigg, K., "La Profilassi e la terapia delle malattie venose degli arti inferiori mediante la compressione con fasciature e con calze elastiche", Minerva Ginecologica, vol. 16, No. 19, pp. 817-823, Oct. 15, 1964.

Sigg, K., "New Approaches to the Treatment of Thrombosis", Angiology—The Journal of Vascular Diseases, vol. 8, No. 1, pp. 44-59, Feb. 1957.

Sigg, K., "Newer Aspects of the Technique of Treating Varicosities", Therapeutishce Umschau, vol. 6, pp. 127-134, Dec. 1949.

Sigg, K., "Phlebosclerosation: experience and results", Der Chirurg, vol. II, No. 40, pp. 487-491, 1969.

Sigg, K., "Prevention and Treatment of Thromboembolic Complications", Wiener Medizinische Wochenschrift, No. 10, pp. 206-213, Mar. 1958.

Sigg, K., "Quick Treatment—a modified Method of Sclerotherapy of Varicose Veins", Zur Diskussion gestellt—Open for Discussion, VASA, vol. 4, No. 1, pp. 73-78, 1975.

Sigg, K., "Sclerotherapy in the Treatment of Varicose Veins", Internist, pp. 388-398, 1967.

Sigg, K., "Technical Details about Injecting Varices", Med. Klin., vol. 67, No. 27/28, pp. 955-959, 1972.

Sigg, K., "The Ambulatory Treatment of Phlebitis", Schwiezerische Medizinische Wochenschrift, vol. 80, No. 2, Jan. 1950.

Sigg, K., "The Foamed Rubber Compression for Phlebitis and for Phlebitic and Varicose Complications", Die Medizinische, No. 27-28, pp. 910-915, Jul. 1952.

Sigg, K., "The Treatment of Leg Ulcers", Die Medizinische, No. 17, pp. 646-648, 1955.

Sigg, K., "The Treatment of Varicosities and Accompanying Complications", Angiology, The Journal of Vascular Diseases, vol. 3, No. 5, pp. 355-379, Oct. 1952.

Sigg, K., "Therapeutic Issues—On the Treatment of Vein Thrombosis with Butazolidin", Schweizerische Medizinische Wochenschrift, $65^{th}$ year of the edition, No. 11, pp. 261-262, Mar. 12, 1955.

Sigg, K., "Treatment of Superficial and Deep Thrombosis and the Application of Butazolidine", Gynaecologia, Supplementum ad vol. 144, pp. 19-23, Jul. 2-4, 1956.

Sigg, K., "Treatment of Varices, varicose ulcer and thrombosis", Vienna Medical Weekly Journal, No. 6, Feb. 11, 1961.

Sigg, K., "Treatment of Varicose Veins in 2-5 days", Dermatologica, vol. 129, No. 2, pp. 111-117, 1964.

Sigg, K., "Varicose Veins and Deep Seated Chronic Leg Vein Thrombosis" Münchener Medizinische Wochenschrift, vol. 98, No. 8, pp. 260-263, Feb. 1956.

Sigg, K., "Varicosis and Thrombosis during Pregnancy, birth and in childbed", Zentralblatt für Gynäkologie, No. 8, pp. 254-259, Feb. 23, 1963.

Singh, I., "Life Without Breathing", Arch. int. Pharmacodyn., vol. CXXXVII, No. 3-4, pp. 318-330, 1962.

Smith, P. Coleridge, "Foam Sclerotherapy in Treatment of Varicose Veins: Results from Europe", Invited Presentation at Pacific Vascular Symposium, Kona, Nov. 2002.

Somer-Leroy, R. de et al., "Echographie du Creux Poplite Recherche D'Une Arteriole Petite Saphene Avant Sclerotherapie", Phlebologie, vol. 44, No. 1, pp. 69-78, 1991.

Steffey, E. et al., "Nitrous Oxide Intensifies the Pulmonary Arterial Pressure Response to Venous Injection of Carbon Dioxide in the Dog" Anesthesiology 52: 52-55, 1980.

Steinacher, J. et al., "Path and Retention Time of a Contrast Medium in the Superficial Venous System under the Conditions of Varix Obliteration. A Study on the method of varix obliteration", Zsch. Haut-Geschl, vol. 43, No. 9, pp. 369-376, 1968.

Steinberg, M. H., "Evaluation of Sotradecol in Sclerotherapy of Varicose Veins", Angiology The Journal of Vascular Diseases, vol. 6, No. 6, pp. 519-532, Dec. 1955.

Stemmer, B. et al., Phlebologie, vol. 22, No. 2, pp. 151-172, Apr.-Jun. 1969.

Stemmer, B., "Comparison of Common Sclerosing Techniques", Zentralblatt für Phlebologie, vol. 3, pp. 170-176, 1970.

Stern, W., "Varicose Veins", The Medical Journal of Australia, vol. II, No. 18, pp. 849-852, Oct. 29, 1960.

Syllabus & Scientific Abstracts of the UIP World Congress Chapter Meeting, San Diego, California, Aug. 27-31, 2003.

Takats, G. de et al., "Aneurysms: General Considerations", Angiology, The Journal of Vascular Disease, vol. 5, No. 3, pp. 173-208, Jun. 1954.

Takats, G. de et al., "Division of the Popliteal Vein in Deep Venous Insufficiency of the Lower Extremities", Society for Vascular Surgery Issue, vol. 29., No. 3, pp. 342-354, Mar. 1951.

Takats, G. de et al., "Ligation of the Saphenous Vein", A report on Two Hundred Ambulatory Operations, Archives of Surgery, vol., 26, No. 1, pp. 72-88, Jan. 1933.

Takats, G. de et al., "The Injection Treatment of Varicose Veins", Surgery, Gynecology and Obstetrics, vol. L, No. 3, pp. 545-561, Mar. 1930.

Takats, G. de, "Ambulatory Ligation of the Saphenous Vein", The Journal of the American Medical Association, vol. 94, No. 16, pp. 1194-1197, Apr. 19, 1930.

Tessari, L., "New Technique for Obtaining Sclero-Foam," Phlebologie, 2000, 53, No. 1, 129.

Tessari, L., "The Tourbillon Turbulence," in Foam Sclerotherapy State of the Art, ed. J.P. Heneriet, editions Phlébologique Francais pp. 51-55 (2002).

The Airspray Foamer Components.

Thibault, P. et al., "Recurrent Varicose Veins", Phlebology, vol. 18, pp. 895-900, 1992.

Tournay, R., Indication of the Exclusive Sclerotherapy or the Consecutive Combination Therapy Surgery-Sclerotization of Varicose Veins, Zentralblatt für Phlebologie, vol. 4, No. 1, pp. 133-142, Feb. 15, 1965.

Tunick, I.S. et al., "Sodium Morrhuate as a Sclerosing Agent in the Treatment of Varicose Veins", Annals of Surgery, vol. XCV, pp. 734-737, 1932.

Tunnicliffe, F.W. et al., "The Intravenous Injection of Oxygen Gas as a Therapeutic Measure", Lancet, vol. II, pp. 321-323, 1916.

Vacheron, J and P, "Essential Varicose Veins on Lower Limbs: Sclerosant Treatment by Streaming", Archives of Cardio-Vascular Diseases, 7$^{th}$ Year, No. 12, pp. 1033-1038, Dec. 1954.

Varshavskii, B. Ya, "Mechanism of Changes in Renal Activity Following intravenous oxygen", vol. 53, No. 2, pp. 173-177, 1967.

Vasdekis, S. N. et al., "Evaluation of non-invasive and invasive methods in the assessment of short saphenous vein termination", Br. J. Surg., vol. 76, pp. 929-932, 1989.

Vin, F., "Echo-Sclerotherapy of the Small Saphenous Vein", Phlébologie, vol. 44, No. 1, pp. 79-84, 1991.

Voss, F., "Special Methods in the Sclerotherapy of Venous Leg Maladies", Zeitschrift für Haut-und Geschlechts-Krankheiten, vol. XXVII, No. 9, pp. 304-306, 1960.

Wefers, H. et al., "Results of Injection Treatment with Regard to Extreme Varication", Zentralblatt für Chirurgie, Issue No. 43, pp. 1825-1828, 1952.

Weindorf, N. et al., "Control of Sclerosis—Treatment for Varicose Veins", Phlëbologie, vol. 43, No. 4, pp. 681-689, 1990.

Wesener, G., "Morphology and new therapies for starburst varicosis and essential telangiectasia", Berufs-Dermatosen, vol. 17, No. 5, pp. 273-281, Oct. 1969.

Westhues, Von H. et al., "The Varicose Symptom Complex", Medizinische Klinik, No. 16, pp. 657-660, 1957.

Weston, R. E. et al., "The Influence of Denitrogenation on the Response of Anesthetized Dogs to Intravenously Injected Oxygen", vol. 26, pp. 837-848, 1946.

Wiedmann, A., "The Varicose Symptom Complex", Report on the Literature from the years 1955-1960, Part 1, Varices, Der Hautarzt, vol. 12, No. 9, pp. 385-391, Sep. 1961.

Wiedmann, Von A., "Varicose Veins", Der Hautarzt, Year 12, No. 10, pp. 433-438, Oct. 1961.

Willenegger, H. et al., "Attempt at carrying out Thromboembolism Propylaxis without Anticoagulants", Schweizerische Medizinische Wochenschrift—Journal Suisse de Medecine, vol. 87, Supplement for No. 24, pp. 739-748, 1957.

Wollmann, Dr. J. C. et al.; Evaluation of the Test; Kreussler Pharma; pp. 17-28, Jan. 29, 2003.

Wollmann, J., "60 years of Sclerosing Foam" Phlebologie 2, p. 63-70, 2004.

Wollmann, J., "The History of Sclerosing Foams" Dermatol. Surg. 2004; 30:694-703.

Zingg, R., "Experimental tests with the new sclerosing agent "Geigy"", pp. 1-9, 1948.

Sigg, K., "Die Varizentherapie," *Deutsche Medizinische Wochenschrift*, No. 15, pp. 665-666, Apr. 9, 1965 (Eng. Translation—"Varicose Vein Therapy").

Wollmann, J.C., "Sclerosant Foams: Stabilities, Physical Properties and Rheological Behavior," *Phlebologie*, pp. 208-17 (Apr. 2010).

Hohler, R. "*Characterization of the bubble size distribution in sclerosant foams*".

Eckmann, D.M., "*Microvascular embolization following polidocanol microfoam sclerosant administration*," Dermatol. Surg. vol. 31 pp. 636-43 (Jun. 2005).

Forlee, M•V., "*Stroke after varicose vein foam injection therapy*," J. Vasc. Surg. vol. 43 pp. 162-64 (Jan. 2006).

Eckmann, D.M., "*Regarding 'Stroke after varicose vein foam injection therapy*,'" J. Vasc. Surg. vol. 44 p. 225 (Jul. 2006).

O'Hare, J,L. "The use of foam sclerotherapy for varicose veins: A survey of the members of the Vascular Society of Great Britain and Ireland," Eur. J. Vasc. Endovasc, Surg, vol. 34: 232-35 (2007).

Sebba, F., "*Chapter 5: Colloidal gas aphrons,*" Foams & Biliquid Foams-Aphrons pp. 63-78 (1987).

Raven, J.P., "*Dry micrfoams: formation and flow in a confined channel*," Eur, Phys. J. B. vol. 51 pp. 137-143 (2006).

Belcaro, G., "*Foam-sclerotherapy, surgery, sclerotherapy, and combined treatment for varicose veinsL A 10-year, prospective, randomized, controlled trial (VEDICO\* Trial)*," Angiology vol. 54 pp. 307-315 (2003).

Hamel-Desnos, C. "*Efficacy of sclerosing foams: summary of the main published clinical trials*," Angeologie vol. 56 pp. 39-44. (2004).

Ganan-Calvo, A.M. "*Coarsening of monodisperse wet microfoams*," Applied Physics Letters vol. pp. 4989-4991 (Jun. 2004).

Rush, J.E., "*Neurological and visual symptoms following treatment of the great saphenous vein with two formulations of polidocalnoi endovenous microfoam*." Phlebology vol. 24 pp. 85-95 (2009).

Sylvoz, N. "*Polidocanol induced cardiotoxicity: a case report and review of the literature*," J. des Maladies Vasculaires vol. 33 pp. 234-238 (2008).

Guex, J., "*Immediate and midterm complications of sclerotherapy: report of a prospective multicenter registry of 12,173 sclerotherapy sessions*," Dermatol. Surg. vol. 31 123-28 (2005).

Simpson, P. "D1 Syringe," (Oct. 13. 2008).

Biegeleisen, H., "*Fatty Acid Solutions for the Injection Treatment of Varicose Veins*," Annals of Surgery, vol. CV, pp. 610-615 (1937).

Barry et al., "Atmosphere, weather, and climate," Taylor & Francis, 3$^{rd}$ Ed., p. 25 (1976).

Luke, J.C., "The Management of Recurrent Varicose veins," *Surgery, Original Communications*, vol. 35, No. 1, pp. 40-44, Jan. 1954.

Communication from the Examining Division of the European Patent Office in EP04798564, dated Apr. 26, 2007.

Reply to Communication from the Examining Division of the European Patent Office in EP04798564, dated Jan. 18, 2008.
Elias, Steve, "Is There a Leak? Where Is the Leak? How Many Leaks? Which Leak Do I Fix?," American College of Phlebolooy, Marcoisland Nov. 7-9, 2008.
Rathbun, Suman, "Venous Thromboembolism: The Problem," American College of Phlebology, Marcoisland Nov. 7-9, 2008.
Pittalugap, Paul, "The Complex Case," American College of Phlebology, Marcoisland Nov. 7-9, 2008.
Wakefield, Thomas, "Diagnosis and Management of PE," American College of Phlebology, Marcoisland Nov. 7-9. 2008.
Guex, J-Jerome, "The French Polidocanol Registry on Long Term Side Effects: A Survey Covering 3357 Patient Years," American College of Phlebology, Marcoisland Nov. 7-9, 2008.
Fronek, Helane, "Treatment of Small Veins," American College of Phlebology, Marcoisland Nov. 7-9. 2008.
Schul, Marlin, "Compression Therapy vs. Sclerotherapy for Isolated Refluxing Reticular Veins and Telangiectasia: 12 Month Results of a Randomized Trial," American College of Phlebology, Marcoisland Nov. 7- 9, 2008.
Schliephake, Dorothee, "A New Standard Digital Imaging System to Document Treatment Success After Sclerotherapy of C1 Varicose Veins Applied in a Double-Blind, Randomized, Controlled Clinical Trial (EASI Study)," American College of Phlebology, Marcoisland Nov. 7-9, 2008.
Wright, David, "A Single Center Pilot Study of Polidocanol Endovenous Microfoam (PEM) Treatment to Evaluate Presence and Durability of Gas Emboli Using Echocardiography," American College of Phlebology, Marcoisland Nov. 7-9, 2008.
Comerota, Anthony, "Management of Acute DVT," American College of Phlebology, Marcoisland Nov. 7-9, 2008.
Stoughton, Julianne, "Basic Sclerotherapy," American College of Phlebology, Marcoisland Nov. 7-9, 2008.
Hill, Douglas, "Comparison of Sclerosant Foam Stability by Foam Composition," American College of Phlebology, Marcoisland Nov. 7-9, 2008.
Morrison, Nick, "Foam Safety Studies," American College of Phlebology, Marcoisland Nov. 7-9, 2008.
Rabe, Eberhard, "Polidocanol, Sodium Tetradecyl Sulfate and Placebo for Sclerotherapy of C1-Varicose Veins," American College of Phlebology, Marcoisland Nov. 7-9, 2008.
Gibson, Kathleen, "Proprietary Polidocanol Endovenous Microfoam Bubble Embolization Does Not Cause Cerebral Injury," American College of Phlebology, Marcoisland Nov. 7-9, 2008.
Slutsky, Eileen, "Sclerotherapy Complications Matting, Staining and Lack of Improvements," American College of Phlebology, Marcoisland Nov. 7-9, 2008.
Gillet, JL, "Side Effects and Complications of Foam Sclerotherapy of the Great and Small Saphenous Veins: a Controlled and Multicentre Prospective Study Including 1025 Patients," American College of Phlebology, Marcoisland Nov. 7-9, 2008.
Morrison, Nick, "Strategies for Preventing the Big, Bad Complications," American College of Phlebology, Marcoisland Nov. 7-9, 2008.
Krusch, Michael, "Insurance and Coding for the Phlebology Practice," American College of Phlebology, Marcoisland Nov. 7-9, 2008.
Caprini, Joseph, "Direct Factor X Inhibition," American College of Phlebology, Marcoisland Nov. 7-9, 2008.
Caprini, Joseph, "DVT Prophylaxis: What Every Physician Should Know," American College of Phlebology, Marcoisland Nov. 7-9, 2008.
Neuhardt, Diana, "Emboli Detection in the MCA Concurrent With Treatment of LE Superficial Venous Insufficiency with Foam Sclerotherapy," American College of Phlebology, Marcoisland Nov. 7-9, 2008.
King, Ted, "Off Label and/or Non-FDA Approved Drugs," American College of Phlebology, Marcoisland Nov. 7-9, 2008.
Frullini, Alessandro, "Sclerosing Foam," American College of Phlebology, Marcoisland Nov. 7-9, 2008.
Meissner, Mark, "Pelvic Veins and Vascular Malformation," American College of Phlebology, Marcoisland Nov. 7-9, 2008.
Schul, Marlin, "Insurance Denials," American College of Phlebology, Marcoisland Nov. 7-9, 2008.
Harper, Kenneth, "Advances in Therapy for Venous Disease Ambulatory Phlebology 'Cleaning Up Branch Varicose veins," American College of Phlebology, Marcoisland Nov. 7-9, 2008.
Rush, Janet, "Neurological and Visual Symptoms Following Treatment of the Saphenous Veins with Two Formulations of Polidocanol Endovenous Microfoam," American College of Phlebology, Marcoisland Nov. 7-9, 2008.
Wakefield, T., "New Anticoagulants, (Total US 2002 VTE Events)" American College of Phlebology, Marcoisland Nov. 7-9, 2008.
Proebstle, Thomas, "One and Two Years Follow-Up of Radiofrequency Segmental Thermal Ablation (RSTA) of Great Saphenous Veins," American College of Phlebology, Nov. 7-9, 2008.
Cabrera, J., "Sclerosants in Microfoam," International Angiology, 2001, 322-329.
Frullini, A., "New Technique in Producing Sclerosing Foam in a Disposable Syringe," Dermatol Surg. 2000, 26, 705-706.
Tessari, L., "Preliminary Experience with a new Sclerosing Foam in the Treatment of Varicose Veins," Dermatol surg. 2001, 27, 58-60.

* cited by examiner

INJECTABLES IN FOAM, NEW PHARMACEUTICAL APPLICATIONS

RELATED APPLICATIONS

Cross Reference to Related Application

This application is a continuation of application Ser. No. 11/342,394, filed Jan. 30, 2006 now abandoned, which in turn is a continuation of application Ser. No. 10/774,071, filed Feb. 6, 2004 now abandoned, which in turn is a continuation of PCT/ES01/00371, filed Aug. 8, 2001.

INTRODUCTION

Parenteral administration is carried out through the skin barrier, in order to introduce medicaments in tissues or organ cavities that are not directly communicated with the exterior and even to introduce them directly into the blood stream, which acts as a distribution system.

One benefit of injectables is their rapid action (almost instantaneous in intravenous administration because the medicinal substances are immediately distributed by the blood) but it can be difficult to maintain this action locally for a given time, above all in highly vascularised areas. Furthermore, it can be laborious to achieve therapeutic concentrations of a substance in poorly vascularised areas or at sites where the traditional distribution via the bloodstream is inadequate to achieve the necessary concentrations of a medicament or to retain the medicament in the selected area for the requisite time for its action to have effect.

With the drug delivery system of injectable foam we achieve a more prolonged local action, also in richly vascularised organs and even in blood vessels. Moreover, the steerability of this pharmaceutical form makes it difficult for the action to reach undesired zones.

Furthermore, the micronisation of the medicinal substances that is produced when we place them on bubbles exponentially increases their active surface area, with the result that the same therapeutic effect is achieved with lower doses. Another benefit conferred by this pharmaceutical form is the possibility of observing ultrasonographically where the medicament is sited.

This drug delivery system may be of interest in the treatment of multiple diseases where the local action of the drugs and medicinal substances injected is of value and cannot be achieved with the pharmaceutical forms in current use.

State of the Previous Technique

According to patent EP,A, 0 077 752 (SCHERING AKTIENGESELLSCHAFT) 1983, liquid mixtures with physiologically compatible gas bubbles have been used as a contrast medium in ultrasound diagnosis.

There have also been attempts, according to patent WO,A, 92 05806 (SINTÉTICA S. A.) 1992, to obtain more stable suspensions of microspheres filled with gas in aqueous liquids, suitable for injection as a medium to increase the echogenicity of the blood and reinforce the ability of ultrasonography to aid medical diagnoses, as for example in the detection of vascular diseases.

Microfoam containing sclerosants has also been injected for the treatment of varicose veins and outcomes have been observed to be superior to those obtained with liquid sclerosants. (WO 95/00120 J. CABRERA GARRIDO, 1995).

Preparation

This invention refers to the preparation of an injectable foam with any medicinal substance, adding foaming agents and gases and producing it in accordance with the conditions required.

In some diseases to be treated, the therapeutic agent can be the gas used in the formation of the foam.

The foam can be produced A) by mechanical or ultrasonic whisking of the solution, B) by depressurisation of a solution that incorporates gas dissolved under pressure, C) after the release of a gas contained in a compartment that is independent of the solution to be foamed and that is released and placed in contact with the solution at the moment of its use, D) through a chemical reaction that produces the gas, etc.

In U.S. Pat. No. 4,446,442, EP-A-131 540, U.S. Pat. No. 4,276,885, procedures are revealed to manufacture solutions of microcapsules or hollow microparticles filled with gas, i.e., microspheres in which the gas is strictly encapsulated. These procedures seek a stability of the microspheres once they are injected into the blood, which allows them to resist their destruction on their intravascular journey and thus to be detected by ultrasonography in vessels that are distant from the injection site. The high stability of these suspensions of microspheres is a necessary condition for their diagnostic efficacy.

Our invention is not attempting to achieve this, but rather to transform into foam any medicinal substance in the presence of gases and foaming agents, but without this producing a dispersion of the microbubbles, which, by continuing to be united by an immaterial boundary, form a different physicochemical entity from solutions of microparticles.

Optionally, it may be of value to improve the cohesion between the bubbles with rheologic agents.

Applications

Injectable foam is of utility, among other cases, in hepatic or renal insufficiency, or in the administration of drugs with little therapeutic margin, such as cytostatics, where we wish to achieve the maximum efficacy of the medicaments with the lowest possible dose delivered as closely as possible to the target tissue.

In localised tumours, the injection of antiinflammatories or corticosteroids in foam may reduce the gastrointestinal risks produced by these agents when they are systemically administered.

In the same way, foam is beneficial in the intravenous use of medicinal substances, for example to promote the local vasodilatation of an ischaemic foot, facilitating the continuance of the injected drug in this zone for the longest possible time.

In abscesses or localised infections, we achieve with injectable foam a more prolonged action of antibiotics or chemotherapeutic antiviral agents in situ, rendering them more efficacious than when they are administered traditionally.

In cases of tinea unguium, given the difficulty of achieving a satisfactory action with systemic administration, it may be of interest to inject beneath the nail foam that contains antimycotic agents.

Another application of injectable foam may be in local anaesthesia, facilitating the diffusion or delaying the distribution of the anaesthetic and thus reducing the repetition of doses.

Moreover, when the therapeutic agent is a gas, it can be maintained in contact at the required site, formed into an injectable foam with inert substances. This would be the case of the administration of oxygen in gas gangrene produced by anaerobic germs or in severe ischaemia of the extremities.

The foam may also be of special utility when the blood cannot be the transport vehicle of a medicament and when an especially intense or selective local action is required, e.g., the in situ use of fibrinolytics/thrombolytics at an adequate concentration in the centre of a thrombosis of an important venous trunk.

To summarise, when it is necessary to maintain the action of an injectable medicament in a given territory, the foam form can provide an increase in its local therapeutic activity, in function of the longer time of its presence, of the reduced dilution at the site required and of the greater active surface area of the medicament.

The invention claimed is:

1. A foam comprising a liquid phase and a gas phase; wherein the liquid phase comprises at least one medicinal agent selected from the group consisting of fibrinolytics and thrombolytics and the liquid phase does not comprise encapsulated microspheres; wherein the at least one medicinal agent is present in a concentration effective to treat a thrombosis; wherein the at least one medicinal agent is not a sclerosing agent; and wherein the foam is not a dispersion of microbubbles in the liquid phase at the time of injection into a patient.

2. The foam of claim 1, wherein the liquid phase further comprises at least one foaming agent.

3. A method of treating a thrombosis comprising injecting an effective amount of a foam into a patient in need thereof and contacting the site of the thrombosis with the foam; wherein the foam comprises a liquid phase and a gas phase; wherein the liquid phase comprises at least one medicinal agent chosen from fibrinolytics and thrombolytics and the liquid phase does not comprise encapsulated microspheres; wherein the at least one medicinal agent is present in a concentration effective to treat a thrombosis; wherein the at least one medicinal agent is not a sclerosing agent; and wherein the foam is not a dispersion of microbubbles in the liquid phase at the time of injection into a patient.

4. The method of claim 3 wherein the liquid phase further comprises at least one foaming agent.

* * * * *